United States Patent [19]
Guillemet et al.

[11] Patent Number: 5,389,092
[45] Date of Patent: Feb. 14, 1995

[54] NON-ADHESIVE HEALING DRESSING

[75] Inventors: Alain Guillemet, Fontaine lés Dijon; Philippe Janod, Dole, both of France

[73] Assignee: Laboratoires d'Hygiene et de Dietetique (L.H.D.), Paris, France

[21] Appl. No.: 903,520

[22] Filed: Jun. 24, 1992

[30] Foreign Application Priority Data

Jul. 3, 1991 [FR] France .................. 91 08305

[51] Int. Cl.$^6$ ............ A61F 13/00; A61F 15/00
[52] U.S. Cl. ....................... 604/304; 602/51; 604/307; 424/447
[58] Field of Search ............ 424/445, 446, 447; 427/2; 602/48, 51; 604/304, 307, 336

[56] References Cited

U.S. PATENT DOCUMENTS

| | | | |
|---|---|---|---|
| 2,464,755 | 3/1949 | Taub | 604/304 |
| 3,339,546 | 9/1967 | Chen | 128/156 |
| 4,231,369 | 11/1980 | Sorensen et al. | 128/283 |
| 4,294,820 | 10/1981 | Keith et al. | 424/28 |
| 4,311,759 | 1/1982 | Glennon | 428/462 |
| 4,538,603 | 9/1985 | Pawelchak et al. | 424/447 |
| 5,154,706 | 10/1992 | Cartmell et al. | 602/48 |

FOREIGN PATENT DOCUMENTS 559027  9/1942  United Kingdom ............ 424/446

*Primary Examiner*—Paul Prebilic
*Attorney, Agent, or Firm*—Jacobson, Price, Holman & Stern

[57] ABSTRACT

The present invention relates to a dressing comprising a mixture of block copolymer with a saturated central sequence and plasticizer. The saturated central sequence has three sequences wherein the structure at each block is a polystyrene terminal block and the central sequence is a saturated polyolefin block.

7 Claims, 1 Drawing Sheet

NON-ADHESIVE HEALING DRESSING

FIELD OF INVENTION

The present invention relates to a novel healing dressing comprising a mixture of block copolymers with a saturated central sequence, and a plasticizer.

BACKGROUND OF INVENTION

The principal families of dressings are dry gauzes, tulles gras, occlusive films and absorbent occlusive dressings. The primary function of all these dressings is to cover the wound and protect it from the external environment, in particular from mechanical, thermal, chemical and bacterial aggression.

SUMMARY OF INVENTION

In addition to possessing the afore-mentioned properties, dry gauzes serve to absorb the exudates. A major disadvantage of this type of dressing is the formation of a foreign body granuloma caused by the release of microfragments of the cotton web into the wound, generating a significant inflammatory response. Another disadvantage is the drying-out of the wound, the consequence of which, when the dressing is removed, is to destroy the regenerated tissues, thus resulting in delayed healing.

It has been proposed to coat dry gauze with a greasy substance in order to reduce its adhesion. Tulles gras thus consist of a dry gauze coated with mineral oils, especially petrolatum. However, on contact with the wound, the petrolatum softens because of the rise in temperature, and tends to be pushed out to the periphery of the dressing. This phenomenon is exacerbated in the presence of exudates and leaves the textile fibers of the tulle in direct contact with the wound, as in the case of dry gauze. Healing then takes place in a semiocclusive environment, the principal direct consequences of which are a decrease in evaporation of the exudates, an increase in humidity and local temperature, a favoring of débridement, the absence of crust formation, a stimulation of granulation and a favoring of microbial multiplication. Finally, delayed healing is observed under a tulle gras.

As occlusion has a favorable action on healing, occlusive films have been proposed, for example the OPSI-TE ® dressing consisting of an adhesive polyurethane film. Reference may usefully be made in this connection to French patent application B-2 012 584. The essential disadvantage of such a dressing is its inability to absorb the exudates, thus resulting in a risk of maceration of the wound, rupture of the dressing and development of a pathogenic bacterial flora.

Absorbent occlusive dressings have also been proposed, in particular hydrocolloidal dressings consisting essentially of carboxymethyl cellulose, pectin and gelatin. Reference may usefully be made in this connection to U.S. Pat. No. 3,339,546 and French patent application B-2 495 473. By virtue of its composition, the adhesive mass of such dressings is converted to a moist soft gel on contact with the wound, thereby developing a microenvironment favorable to cell multiplication, collagen synthesis, fibrinolysis, angiogenesis and good progression of the wound's bacterial cycle. Despite this favorable microclimate, the results of healing studies on this type of dressing remain divided. Healing is not always accelerated to a significant degree.

Finally, Japanese patent application 54 138 124 has disclosed a dressing which adheres well to the skin but is easy to remove, its matrix being based on a mixture of non-vulcanized block copolymers of the A-B-A type, especially poly(styrene/butadiene/styrene) and poly(-styrene/isoprene/styrene), dissolved in an oily substance. These copolymers differ from the copolymers used within the framework of the present invention by the chemical structure of the central elastomeric sequence, which is unsaturated for the copolymers recommended by Japanese patent application 54 138 124 whereas the present invention recommends copolymers with a saturated central sequence. Furthermore, the healing power of the dressing according to Japanese patent application 54 138 124 is markedly inferior to that of the healing dressing according to the invention, as shown in the comparative tests reproduced in the present description.

A novel technical solution is now proposed which is such that the healing dressing according to the invention protects the wound from the external environment and retains the exudates, thus creating a moist medium favorable to cell growth and multiplication, and does not adhere to the wound, the consequence of which is to avoid traumatizing the wound when the dressing is removed, and to favor epithelialization under good conditions.

The dressing with a matrix containing a block copolymer, according to the invention, comprises in its matrix 10 to 30 parts by weight of a block copolymer with a saturated central sequence, especially polystyrene/polyethylene-butylene/polystyrene, and 70 to 90 parts by weight of plasticizer, especially petrolatum. The mass made up of the mixture of block copolymers with a saturated central sequence, and plasticizer, is non-adhesive.

Block copolymers with a saturated central sequence are understood here as meaning styrene block copolymers with three sequences, the central sequence being saturated. Their structure is such that, at each end, each block consists of a polystyrene terminal block, the central sequence between said terminal blocks consisting of a saturated polyolefin block.

The present invention therefore excludes block copolymers with an unsaturated central sequence which are composed of polystyrene terminal blocks and a central sequence consisting of an unsaturated polyolefin block, for example polystyrene/polybutadiene/polystyrene or polystyrene/polyisoprene/polystyrene copolymers.

Preference will advantageously be given to polystyrene/polyethylene-butylene/polystyrene copolymers (abbreviated to S-EB-S), especially S-EB-S in which the ratio number of styrene units/number of ethylene-butylene units is less than 0.5 and preferably of the order of 0.4. These copolymers are marketed in particular by the Shell Chemical Company under the name Kraton ® G.

Plasticizer is understood here as meaning a liquid or pasty greasy substance, especially mineral oils, liquid or pasty paraffins and silicone oils or greases. Plasticizers with a drop point below 70° C., and more particularly petrolatum with a drop point of between 40° and 60° C., will be preferred.

Advantageously the healing dressing according to the invention consists of a non-adhesive mass comprising 15 to 25 parts by weight of polystyrene/polyethylene-butylene/polystyrene in which the ratio styrene units/ethylene-butylene units is less than 0.5 and preferably of the order of 0.4, and 75 to 85 parts by weight of petrolatum with a drop point of between 40° and 60° C.

Although it is not generally necessary in view of the fact that the mixture of block copolymer with a saturated central sequence, and plasticizer, according to the invention, is a mass of sufficient cohesion, it is possible to add a web embedded in the mass resulting from the mixing of the block copolymer with a saturated central sequence, and the plasticizer. Such a web can consist of natural or man-made fibers, for example woven or nonwoven cotton or polyamide fibers. It is important for the web to be totally embedded in the mass forming the dressing, so as to exclude any possibility of adhesion of the fibers to the wound.

If necessary, the healing dressing according to the invention can be covered with a support, for example polyurethane or polyester films or a woven or nonwoven fabric consisting of natural or synthetic fibers. The purpose of such a support is to protect the dressing according to the invention, the dressing then being applied to the wound or skin with the support on the opposite side from the wound or skin.

An active principle, present in a therapeutically effective amount, can also be added to the mass consisting of the block copolymer with a saturated central sequence, and the plasticizer. Said active principle will be added to said mass either molten, if its melting point is compatible with the mixing temperature of the constituent ingredients of the mass, or solid at a temperature compatible with the mixing temperature of the constituent ingredients of the mass, or else in solution in the plasticizer. Examples of active principles which may be mentioned are steroidal or non-steroidal antiinflammatories, analgesics, antibiotics, antibacterial agents, antifungal agents, antiseptics, surface anaesthetics, proteolytic enzymes, healing adjuvants, growth factors and propolis. The release of the active principle can be accelerated, if necessary, by adding an agent for promoting the release of the active principle. Agents recommended for this purpose are especially polyols and alkylene glycol esters, for example diethylene glycol monoethyl ether or dipropylene glycol. The amount of agent for promoting the release of the active principle will be between 0.1 and 5%, advantageously of the order of 2 to 2.5%, relative to the total weight of the dressing.

The method of preparing a dressing according to the invention consists in mixing the block copolymer with a saturated central sequence, the plasticizer and, if appropriate, the active principle and the agent for promoting the release of the active principle, in a malaxator, at the softening point of the copolymer, malaxating the resulting mixture for about 1 hour, then, at a temperature 10° to 40° C. below the softening point of the copolymer, coating the mixture on to a silicone-treated support, which can be peeled off before use, so as to give a thickness of between 10 $\mu$m and 1 cm, preferably of 100 $\mu$m to 500 $\mu$m, leaving the resulting product to cool and finally cutting it to the desired size. If necessary, the coating step will be carried out in such a way that a web is embedded in the mass made up of the block copolymer with a saturated central sequence, and the plasticizer.

The healing dressing obtained by this method can be packaged in a protective envelope, for example a heat-sealed envelope made of polyterephthalate ester/polyethylene between two shields made of silicone-treated polyester. If necessary, the healing dressing will be sterilized by irradiation with gamma rays at a dose of between 25 and 32 kGy.

The invention will be understood more clearly from the description of the Preparatory Examples and pharmacological tests which follow.

PREPARATION I (Example 1)

42.5 kg of officinal petrolatum marketed under the trademark FINA ® F 7850, with a drop point equal to 57° C., and 15 kg of polystyrene/polyethylene-butylene/polystyrene copolymer marketed by SHELL under the trademark KRATON ® G 1652 (ratio number of styrene units/number of ethylene-butylene units=29/71, i.e. 0.40) are introduced into a malaxator heated to 130° C. The whole is homogenized for 1 hour, a further 42.5 kg of officinal petrolatum FINA ® F 7850 are then incorporated and the whole is homogenized again for 0.5 hour. The mixture obtained, which is fluid and transparent, is coated on to a 40 $\mu$m thick silicone-treated polyester film, at a temperature of 105° C., so as to give a thickness of 400 $\mu$m. The resulting film is cut into 3 cm×6 cm rectangular dressings and each dressing is packaged in a heat-sealed envelope made of polyterephthalate ester/polyethylene and is then sterilized by gamma irradiation at a dose of 25 kGy.

PREPARATION II (Example 2)

The procedure is analogous to that of Preparation I, 37.5 kg of officinal petrolatum FINA ® F 7850 and 25 kg of polystyrene/polyethylene-butylene/polystyrene copolymer KRATON ® G 1652 being introduced into the malaxator, followed by a further 37.5 kg of officinal petrolatum FINA ® F 7850.

PREPARATION III (Example 3)

The procedure is analogous to that of Preparation I, the petrolatum FINA ® F 7850 being replaced with the same amount of petrolatum PROLABO RECTAPUR ®, with a drop point of between 50° and 55° C., marketed by RHONEPOULENC.

PREPARATION IV (Example 4)

The procedure is analogous to that of Preparation I, the polystyrene/polyethylene-butylene/polystyrene copolymer KRATON ® G 1652 being replaced with a polystyrene/polyethylene-butylene/polystyrene copolymer KRATON ® G 1650 (ratio number of styrene units/number of ethylene-butylene units=0.40).

PREPARATION V (Comparative Example 5)

25 kg of paraffin oil marketed under the trademark SIDEPALINE ® BC 015 are introduced into a malaxator heated to 150° C., followed by 5 kg of polystyrene/polybutadiene/polystyrene copolymer marketed by SHELL under the trademark Cariflex ® TR 1101 and 15 kg of polystyrene/polyisoprene/polystyrene copolymer marketed under the trademark Cariflex ® TR 1107. The whole is homogenized for 1 hour, a further 50 kg of paraffin oil are then incorporated and the whole is homogenized again for 0.5 hour. The mixture obtained is coated on to a 40 $\mu$m thick silicone-treated polyethylene film, at a temperature of 125° C., so as to give a thickness of 1 mm, and then laminated with a nonwoven fabric consisting of 55 g/m² of polyester fibers, marketed under the trademark SONTARA ® by Dupont de Nemours. The dressing obtained is then packaged in the same way as the dressing of Example 1.

PREPARATION VI (Example 6)

150 g of the product obtained in Example 1 are heated on a water bath for 1 hour at 90° C. 50 g of a premix, obtained by mixing 250 g of officinal petrolatum FINA ® F 7850 and 250 g of the sodium salt of rifamycin in the cold, are then added. After stirring for 5 minutes, the mixture obtained is run into a boat made of silicone-treated polyester. After cooling, the solid product obtained is extracted from the boat and pressed at 90° C. for 2 minutes to give a 350 μm thick sheet, which is cut into 10 cm×10 cm dressings.

PREPARATIONS VII to XIV (Examples 7 to 14)

The following products were obtained by a procedure analogous to that of Preparation VI:

Example 7: the sodium salt of rifamycin was replaced with the same amount of neomycin sulfate.

Example 8: the sodium salt of rifamycin was replaced with the same amount of ibuprofen.

Example 9: the sodium salt of rifamycin was replaced with the same amount of sodium benzoate.

Example 10: the premix consists of 115 g of officinal petrolatum FINA ® F 7850 and 115 g of benzalkonium chloride.

Example 11: the premix consists of 100 g of officinal petrolatum FINA ® F 7850 and 100 g of lidocaine hydrochloride.

Example 12: the premix consists of 100 g of officinal petrolatum FINA ® F 7850 and 100 g of sodium benzoate.

Example 13: the premix consists of 95 g of officinal petrolatum FINA ® F 7850 and 5 g of triamcinolone.

Example 14: the premix consists of 150 g of officinal petrolatum FINA ® F 7850 and 50 g of econazole nitrate.

The microbiological activity of the products of Examples 6 and 7 was checked in vitro. The products exhibit an antibacterial activity consistent with the European Pharmacopeia.

The dressing according to the invention possesses particularly remarkable healing properties. These healing properties were studied on an animal model of non-retarded healing by comparison with the product of Example 5, consisting of copolymers with an unsaturated central sequence, and by comparison with a 100% cotton dry gauze and a tulle gras marketed under the trademark Tulle Gras Lumière ®.

Each group consists of 10 non-consanguineous WISTAR rats. A 10 cm² (2 cm×5 cm) paravertebral wound is made on one side of each animal. The wound is made under aseptic conditions by dermo-epidermal excision, including the musculus platysma. Immediately after excision, a dressing to be studied (3 cm×6 cm) is applied to the wound so that it is totally covered. The dressing is covered with a sterile gauze and the whole is held with adhesive tape. The dressing is removed every 3 days, the wound is cleansed by rinsing with a sterile solution of sodium chloride and a new dressing is then applied until total healing is obtained. On the day of the excision and then every 3 days up to total healing, the macroscopic appearance of the wound is observed, the wound is photographed under standard conditions and the progress of the wound is analyzed comparatively and quantitatively (perimeter and surface) FIG. 1 shows the percentage of healed animals plotted as a function of time.

BRIEF DESCRIPTION OF DRAWING

The results obtained are shown in FIG. 1, where the percentage (%) of healed animals is plotted on the ordinate as a function of time (expressed in days) on the abscissa. Curve 6 is the one obtained with the dry gauze, curve 7 is the one obtained with the tulle gras Lumière ®, curve 3 is the one obtained with the dressing of Example 3, curve 1 is the one obtained with the dressing of Example 1, curve 2 is the one obtained with the dressing of Example 2, curve 4 is the one obtained with the dressing of Example 4 and curve 5 is the one obtained with Comparative Example 5. The percentage of totally healed animals has been shown as a function of the number of days of healing. The dressings according to the invention make it possible to obtain total healing as from day 18 for the dressings of Examples 1 and 3, day 21 for the dressing of Example 2 and day 24 for the dressing of Example 4. The dressings consisting of dry gauze, tulle gras or copolymers with an unsaturated central sequence do not make it possible to obtain total healing until day 39. The healing power of the dressings according to the invention is therefore distinctly superior to that of the known dressings of the prior art.

Furthermore, it was observed that in the animals treated with dry gauze and tulle gras, the area of the wound increases up to day 3, representing nearly 120% of the initial area of the wound. In the animals treated with the comparative dressing of Example 5, the area of the wound does not change up to day 3. By contrast, in the animals treated with the dressings of Examples 1 to 4 according to the invention, the area of the wound decreases as from day 1, representing no more than 80% of the initial area on day 3. This constitutes a considerable advantage compared with the known dressings of the prior art, especially in the treatment of burns, where it is important to preserve the area of unburnt skin and rapidly increase the area of healthy skin.

Figure 1:
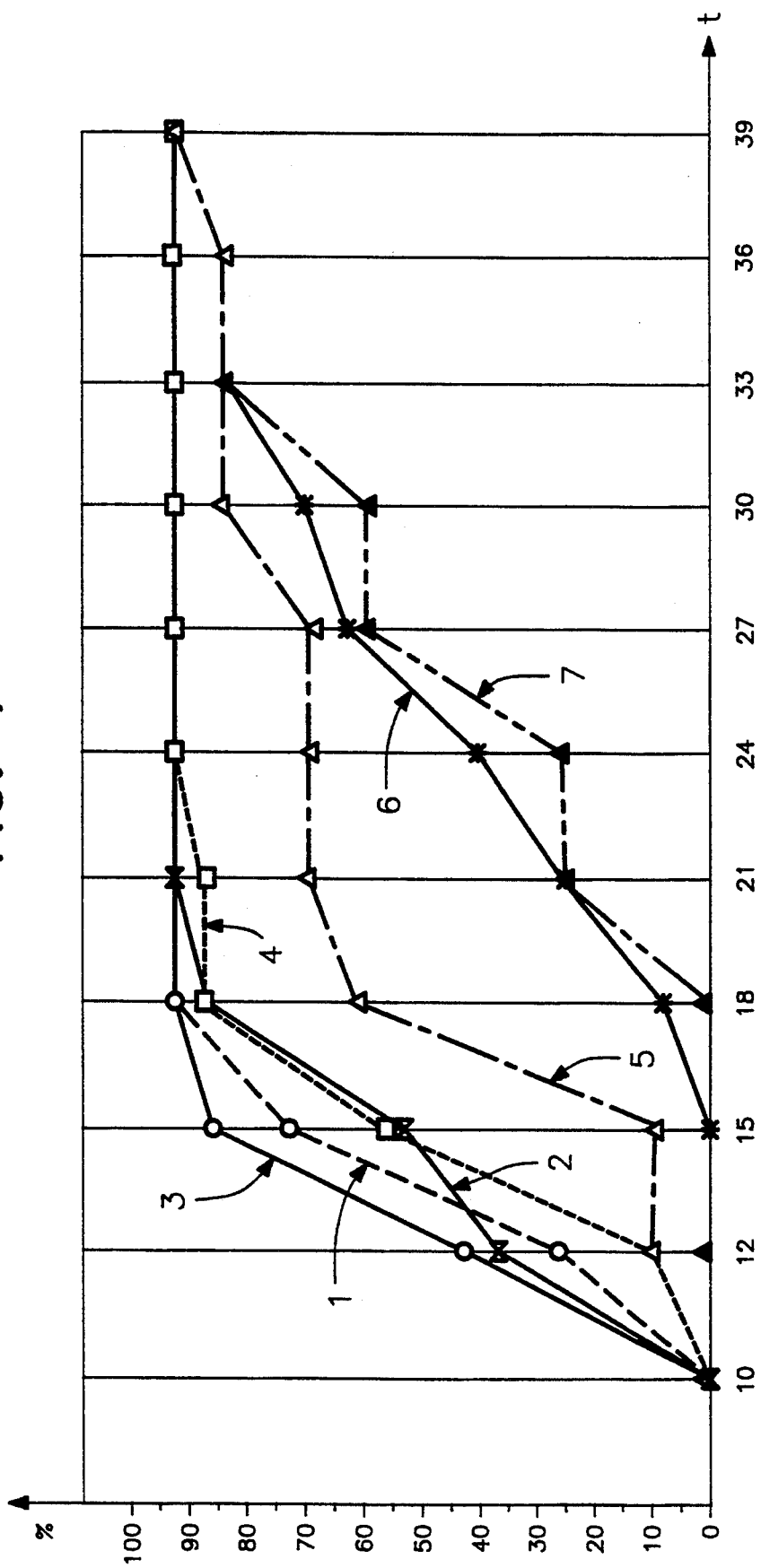

The dressings according to the invention are useful in the care and treatment of wounds and burns in human and veterinary medicine as well as in surgery. They are also useful in the treatment of skin complaints such as, for example, psoriasis, eczema and dermatosis, and wounds of dermatological origin.

What is claimed is:

1. A dressing with a matrix containing a block copolymer, said matrix consisting essentially of 10 to 30 parts by weight of a block copolymer with a saturated central sequence, which is a polystyrene/polyethylene-butylene/polystyrene copolymer, and 70 to 90 parts by weight of a plasticizer which is petrolatum.

2. A dressing according to claim 1 said matrix consisting essentially of 15 to 25 parts by weight of polystyrene/polyethylene-butylene/polystyrene in which the ratio of styrene units/ethylene-butylene units is less than 0.5, and 75 to 85 parts by weight of petrolatum with a drop point of between 40° and 60° C.

3. A dressing with a matrix containing a block copolymer, said matrix consisting essentially of:
   (a) 10 to 30 parts by weight of a block copolymer with a saturated central sequence which is a polystyrene/polyethylene-butylene/polystyrene copolymer;
   (b) 70 to 90 parts by weight of a plasticizer which is petrolatum;
   (c) a therapeutically effective amount of an active principle; and
   (d) a web embedded in the said matrix.

4. A dressing according to claim 3, wherein the active principle is selected from a group consisting of antiinflammatories, analgesics, antibiotics, antifungal agents, antibacterial agents, antiseptics, anaesthetics, proteolytic enzymes, healing adjuvants, growth factors and propolis.

5. A dressing according to claim 1 which also comprises a support covering one face of the matrix.

6. A dressing according to claim 1, said matrix consisting essentially of 15 to 25 parts by weight of polystyrene/polyethylene-butylene/polystrene in which the ratio of styrene units/ethylene-butylene units is less than 0.4 and 75 to 85 parts by weight of petrolatum with a drop point of between 40° to 60° C.

7. A method of using a dressing comprising providing a dressing with a matrix containing a block copolymer, said matrix consisting essentially of 10 to 30 parts by weight of the block copolymer with a saturated central sequence, and 70 to 90 parts by weight of plasticizer;

said block copolymer having 3 sequences wherein the structure at the end of each block is a polystyrene terminal block in the central sequence between said terminal block is a saturated polyolefin block; said method further comprising applying said dressing to the wound or skin of a mammal.

* * * * *